(12) United States Patent
Kato

(10) Patent No.: US 8,525,982 B2
(45) Date of Patent: *Sep. 3, 2013

(54) REFRACTIVE INDEX DISTRIBUTION MEASURING METHOD AND REFRACTIVE INDEX DISTRIBUTION MEASURING APPARATUS

(75) Inventor: Seima Kato, Utsunomiya (JP)

(73) Assignee: Canon Kabushiki Kaisha (JP)

( * ) Notice: Subject to any disclaimer, the term of this patent is extended or adjusted under 35 U.S.C. 154(b) by 36 days.

This patent is subject to a terminal disclaimer.

(21) Appl. No.: 13/114,309

(22) Filed: May 24, 2011

(65) Prior Publication Data

US 2011/0292379 A1 Dec. 1, 2011

(30) Foreign Application Priority Data

May 25, 2010 (JP) ................................. 2010-119636

(51) Int. Cl.
*G01N 21/41* (2006.01)
*G01B 9/00* (2006.01)

(52) U.S. Cl.
USPC .......................................... 356/128; 356/124

(58) Field of Classification Search
USPC .................. 356/124–128, 517–518, 73.1, 30, 356/31
See application file for complete search history.

(56) References Cited

U.S. PATENT DOCUMENTS

| 4,265,534 A | 5/1981 | Remijan |
| 4,541,697 A | 9/1985 | Remijan |
| 4,542,989 A | 9/1985 | Remijan |
| 4,565,449 A * | 1/1986 | Grego ........................... 356/484 |
| 4,744,654 A | 5/1988 | Jinno et al. |
| 4,934,818 A | 6/1990 | Glantschnig et al. |

(Continued)

FOREIGN PATENT DOCUMENTS

| JP | 58-045526 A | 3/1983 |
| JP | 61-070436 A | 4/1986 |

(Continued)

OTHER PUBLICATIONS

Takeda, Mitsuo et al. "Lateral aberration measurements with a digital Talbot interferometer," Applied Optics, vol. 23, No. 11, Jun. 1, 1984, pp. 1760-1764. Cited in related U.S. Appl. No. 12/728,878.

(Continued)

*Primary Examiner* — Gregory J Toatley
*Assistant Examiner* — Shawn Decenzo
(74) *Attorney, Agent, or Firm* — Rossi, Kimms & McDowell LLP

(57) ABSTRACT

A method includes the steps of measuring a first transmitted wavefront in a first medium having a first refractive index and a second transmitted wavefront in a second medium having a second refractive index different from the first refractive index, and obtaining a refractive index distribution projected value of the object in each orientation by removing a shape component of the object utilizing measurement results of the first transmitted wavefront and the second transmitted wavefront and each transmitted wavefront of a reference object that has the same shape as that of the object and a specific refractive index distribution and is located in one of the first medium and the second medium with the same orientation as that of the object, and calculating a three-dimensional refractive index distribution of the object based on a plurality of refractive index distribution projected values corresponding to the plurality of orientations.

11 Claims, 5 Drawing Sheets

(56) References Cited

U.S. PATENT DOCUMENTS

| | | | |
|---|---|---|---|
| 5,151,752 A * | 9/1992 | Oono et al. | 356/128 |
| 5,309,214 A * | 5/1994 | Hashimoto | 356/128 |
| 5,526,118 A * | 6/1996 | Miyagawa et al. | 356/484 |
| 6,765,661 B2 | 7/2004 | Biel et al. | |
| 7,388,676 B2 * | 6/2008 | Sawada | 356/517 |
| 2006/0159332 A1 | 7/2006 | Sawada | |
| 2007/0109555 A1 | 5/2007 | Gustafsson et al. | |
| 2009/0109401 A1 * | 4/2009 | Van Heugten | 351/221 |
| 2009/0147241 A1 | 6/2009 | Shlezinger et al. | |
| 2010/0165355 A1 | 7/2010 | Kato | |
| 2010/0245842 A1 | 9/2010 | Kato | |
| 2011/0134438 A1 * | 6/2011 | Kato | 356/517 |
| 2012/0139136 A1 | 6/2012 | Kato | |
| 2012/0241989 A1 * | 9/2012 | Sugimoto | 264/1.1 |

FOREIGN PATENT DOCUMENTS

| | | |
|---|---|---|
| JP | 1-35282 B2 | 7/1989 |
| JP | 01-316627 A | 12/1989 |
| JP | 02-008726 A | 1/1990 |
| JP | 2-008726 A | 1/1990 |
| JP | 03-128411 A | 5/1991 |
| JP | 03-225259 A | 10/1991 |
| JP | 08-014852 A | 1/1996 |
| JP | 08-304229 A | 11/1996 |
| JP | 11-044641 A | 2/1999 |
| JP | 2005-106835 A | 4/2005 |
| JP | 2005-201724 A | 7/2005 |
| JP | 2006-200999 A | 8/2006 |
| JP | 2010-151578 A | 7/2010 |

OTHER PUBLICATIONS

Takeda, Mitsuo et al. "Fourier-transform method of fringe-pattern analysis for computer-based topography and interferometry," Optical Society of America, Vo. 72, No. 1, Jan. 1982, pp. 156-160. Cited in related U.S. Appl. No. 12/728,878.

Korean Office Action for KR 10-2009-012038, dated Aug. 10, 2012. Cited in related U.S. Appl. No. 12/728,878.

International Search Report issued Aug. 30, 2011 for PCT/JP2011/062041 (cited in related US2012-0241989).

Ranjbar, et al., "Nondestructive Measurement of Refractive Index Profile of Optical Fiber Preforms Using Moire Technique and Phase Shift Method", Optical Communication, vol. 6025, 605250, 2006 (cited in related US2012-0241989).

* cited by examiner

REFRACTIVE INDEX DISTRIBUTION MEASURING METHOD AND REFRACTIVE INDEX DISTRIBUTION MEASURING APPARATUS

BACKGROUND OF THE INVENTION

1. Field of the Invention

The present invention relates to a refractive index distribution measuring method and a refractive index distribution measuring apparatus.

2. Description of the Related Art

Japanese Patent Laid-Open No. ("JP") 01-316627 proposes a method for finding a refractive index distribution of an object by measuring its transmitted wavefront while the object is immersed in a medium (matching oil) which has approximately the same refractive index as that of the object. JP 02-008726 proposes a method for finding a refractive index distribution of an object by measuring its transmitted wavefront while the object is immersed in each of two types of matching oils, which has a slightly different refractive index from that of the object.

These methods disclosed in JPs 01-316627 and 02-008726 need matching oils each of which has approximately the same refractive index as that of the object. However, the matching oil having a high refractive index has a low transmittance, and a detector can output only a weak signal. Thus, the measuring precision of the object having a high refractive index is likely to lower.

SUMMARY OF THE INVENTION

The present invention provides a refractive index distribution measuring method and a refractive index distribution measuring apparatus which can highly precisely measure a refractive index distribution of an object.

A refractive index distribution measuring method according to the present invention includes the steps of measuring a transmitted wavefront of an object by arranging the object in a medium having a refractive index different from that of the object, and by introducing reference light into the object, and calculating a refractive index distribution of the object by using a measurement result of the transmitted wavefront. In a plurality of orientations of the object in the medium which are different from each other, the measuring step measures a first transmitted wavefront in a first medium having a first refractive index and a second transmitted wavefront in a second medium having a second refractive index different from the first refractive index. The calculating step obtains a refractive index distribution projected value of the object in each of the plurality of orientations by removing a shape component of the object utilizing measurement results of the first transmitted wavefront and the second transmitted wavefront and each transmitted wavefront of a reference object that has the same shape as that of the object and a specific refractive index distribution and is located in one of the first medium and the second medium with the same orientation as that of the object. The calculating step then calculates a three-dimensional refractive index distribution of the object based on a plurality of refractive index distribution projected values corresponding to the plurality of orientations.

Further features of the present invention will become apparent from the following description of exemplary embodiments with reference to the attached drawings.

DESCRIPTION OF THE EMBODIMENTS

Referring now to the accompanying drawings, a description will now be given of embodiments of the present invention.

First Embodiment

Figure 1:
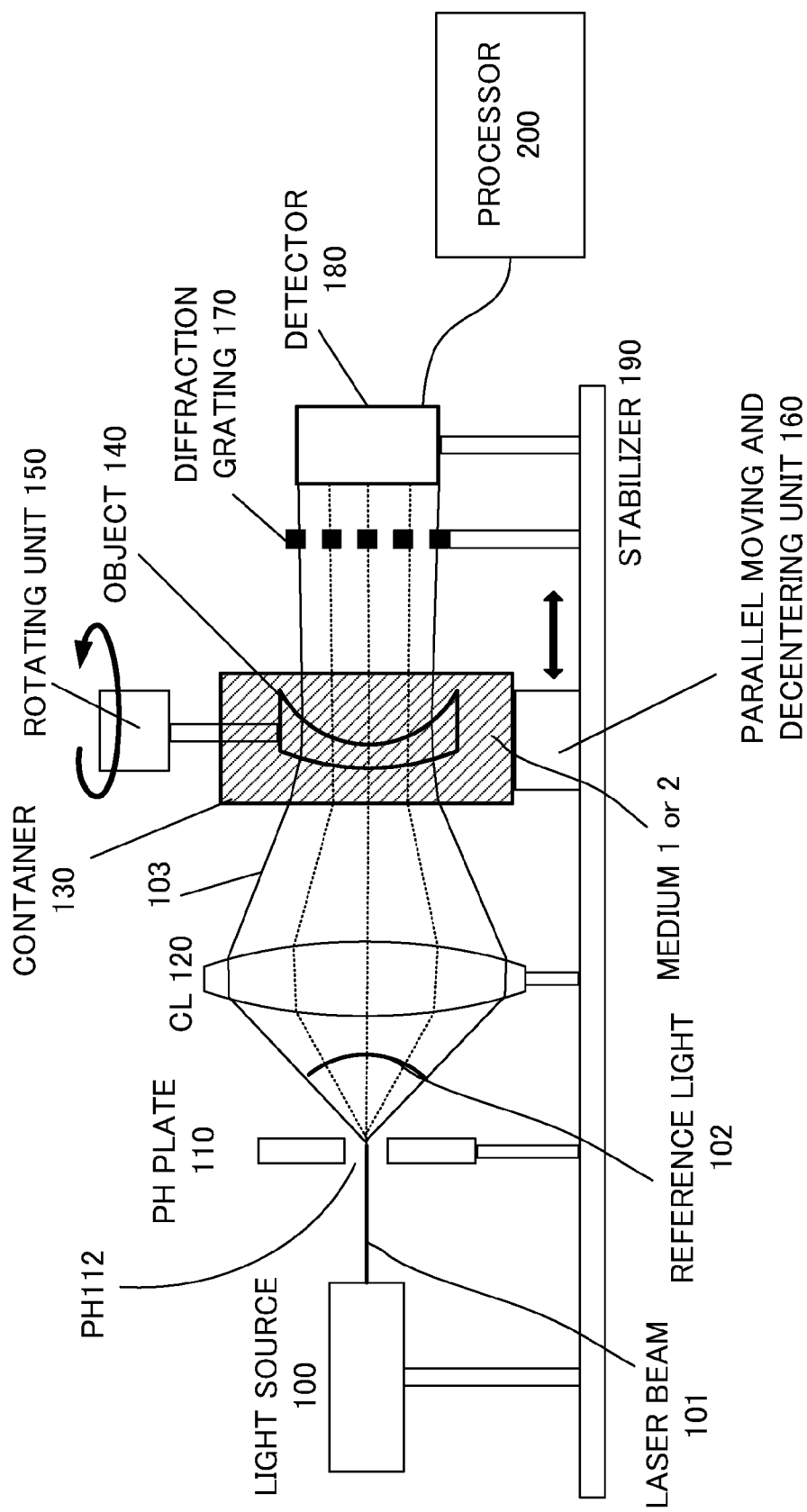
FIG. 1 is a block diagram of a refractive index distribution measuring apparatus according to a first embodiment.

FIG. 1 is a block diagram of a refractive index distribution measuring apparatus installed on a stabilizer 190. The refractive index distribution measuring apparatus measures a transmitted wavefront of an object by immersing the object in each of two types of media, such as air and water, each of which has a refractive index different from that of the object and by introducing reference light from a light source into the object. The refractive index distribution measuring apparatus then calculates a refractive index distribution of the object utilizing a processor as a computer and a measurement result of the transmitted wavefront. This embodiment utilizes a Talbot interferometer as a measuring unit configured to measure the transmitted wavefront of the object arranged in the medium by utilizing the light from the light source.

The object 140 is an optical element, such as a lens. A container 130 houses a medium 1 such as air, or a medium 2 such as water. The refractive index of air or water is smaller than the refractive index of the object 140 by 0.01 or higher.

A laser beam 101 emitted from a laser light source 100, such as a He—Ne laser, along an optical axis is diffracted when it passes through a pinhole (PH) 112 in a pinhole plate (optical member) 110. The diffracted or reference light diffracted in the pinhole 112 is converted into convergent light 103 by a collimator lens (CL) 120.

The convergent light 103 transmits the medium 1 or 2 and the object 140 in the container 130. This embodiment assumes the object 140 to be a rotationally symmetrical lens around an axis. A diameter Φ of the pinhole 112 is so small that the diffracted light 102 can be regarded as an ideal spherical wave, and the diameter Φ is designed to satisfy the following expression using a numerical aperture NAO on the object side and a wavelength λ of the laser light source 100:

$$\Phi \approx \frac{\lambda}{NAO} \qquad \text{Expression 1}$$

When λ is 600 nm and NAO is about 0.3, the diameter Φ of the pinhole 112 may be about 2 μm.

The laser beam that has transmitted the object 140 and air or water in the container 130 passes an orthogonal diffraction grating 170 as a two-dimensional diffraction grating, and is captured (measured) by an image-pickup element (CCD sensor or CMOS sensor) 180. The orthogonal diffraction grating 170 and the image-pickup element 180 will be sometimes referred to as a "sensor" hereinafter.

When the numerical aperture (NA) of the object 140 on the image side is small and a (Talbot) distance Z between the diffraction grating 170 and the image-pickup element 180 satisfies the Talbot condition as represented by Equation 2, the spurious resolution of the diffraction grating 170 is obtained as an interference pattern on the image-pickup element 180, where m is an integer except 0, d is a grating pitch of the diffraction grating 170, $Z_0$ is a distance from the diffraction gratin 170 to the image plane of the object 140. The grating pitch d is determined in accordance with a magnitude of the aberration of the object 140.

$$\frac{Z_0 Z}{Z_0 - Z} = \frac{md^2}{\lambda}$$ Expression 2

The object 140 is configured rotatable around an axis perpendicular to the optical axis by the rotating unit 150, and relatively movable in the optical axis direction by the parallel moving and decentering unit 160. The rotating unit 150 serves as an adjuster configured to adjust an orientation of the object in the medium. The collimator lens 120, the diffraction grating 170, and the image-pickup element 180 are also configured to relatively move on a rail (not illustrated) installed parallel to the optical axis.

Figure 2:
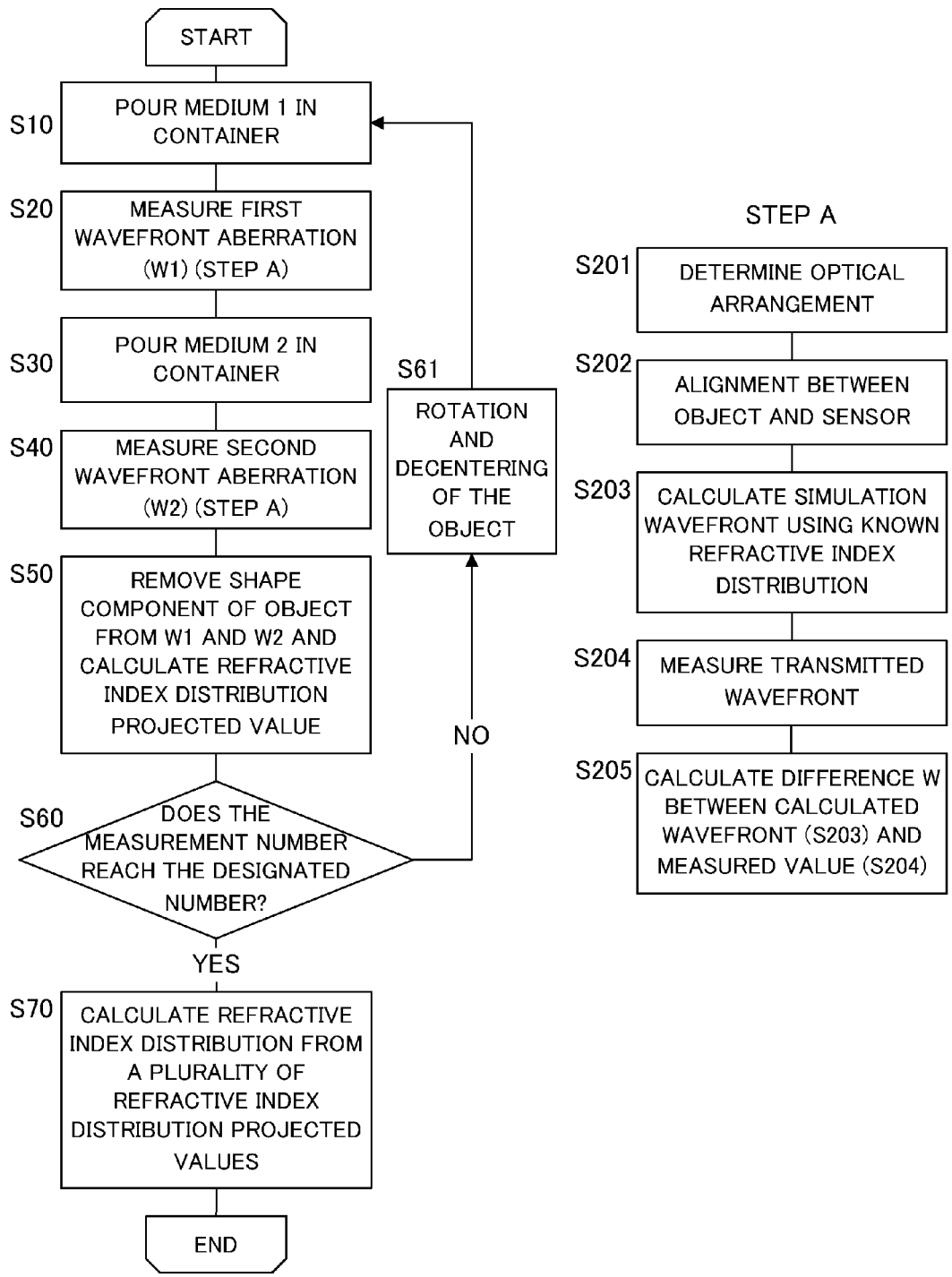
FIG. 2 is a flowchart for illustrating a refractive index distribution measuring method according to the first embodiment.

FIG. 2 is a flowchart for illustrating a refractive index distribution measuring method according to this embodiment, and "S" stands for the step. The refractive index distribution measuring method is executed as a computer program by the processor 200, such as a microcomputer illustrated in FIG. 1.

As illustrated in FIG. 1, the medium 1 (air) as a first medium having a first refractive index is filled in the container 130 (S10).

Next, a (first) wavefront aberration W1 of the object 140 immersed in the medium 1 in the container 130 is measured in accordance with the step A (S20).

The measurement result of the transmitted wavefront contains a refractive index distribution of the object, influence of the object shape, influence of the object shape error, and an offset by the measuring system. Among them, the influence of the object shape and the offset by the measuring system are calculated by simulation and removed from the measurement result of the transmitted wavefront. The step A finds the wavefront aberration W1, and obtains remaining information which contains the refractive index distribution of the object and the influence of the object shape error.

The step A initially determines an optical arrangement of each component, that is, intervals among the pinhole plate 110, the collimator lens 120, the container 130, the diffraction grating 170, and the image-pickup element 180 in the optical axis direction (S201). The optical arrangement is to restrain the NA equal to or lower than about 0.3 and to make appropriate the light flux size on the image-pickup element 180 so as to obtain the spurious resolution of the diffraction grating 170 over the entire surface of the image-pickup element in the Talbot interferometer. The optical arrangement prevents the light fluxes that have passed different positions on the object 140 from converging on the same point on the image-pickup element 180 so as to correlate a position on the image-pickup element 180 with a position on the object 140 in the subsequent steps.

Next, each component is arranged in accordance with the determined optical arrangement and the object 140 is aligned with the sensor (S202). The alignment is performed by a relative movement using the parallel moving and decentering unit 160 in FIG. 1 and/or the relative movements on the rail (not illustrated). The object 140 illustrated in FIG. 1 is a concave lens, but if the object 140 is a convex lens, the container 130 may be installed behind the condensing position of the collimator lens 120 (on the side of the diffraction grating 170) so as to make appropriate the light flux size on the image-pickup element 180.

Next, a simulation wavefront $W_{sim}$ of the transmitted wavefront is calculated by assuming an ideal refractive index distribution (i.e., specific refractive index distribution) that has no refractive index distribution (S203). This embodiment refers to an object having a known shape (which is the same as that of the object in this embodiment) and a known specific refractive index distribution as a reference object, and its transmitted wavefront as a reference transmitted wavefront. In S203, each transmitted wavefront is obtained by arranging the reference object in each of the first medium and the second medium with the same orientation as that of the object.

The known refractive index distribution may be a designed value or a measured value. The simulation wavefront $W_{sim}$ is found based on a relationship of Expression 3 at a coordinate (x, y) of the reference object:

$W_{sim}(x,y)=OP_{sim}(x,y)-OP_{sim}(0,0)$ $OP_{sim}(x,y)=L1(x,y)+L2(x,y)N_1+L3(x,y)Ng+L4(x,y)N_1+L5(x,y)$ Expression 3

Figures 3A, 3B:
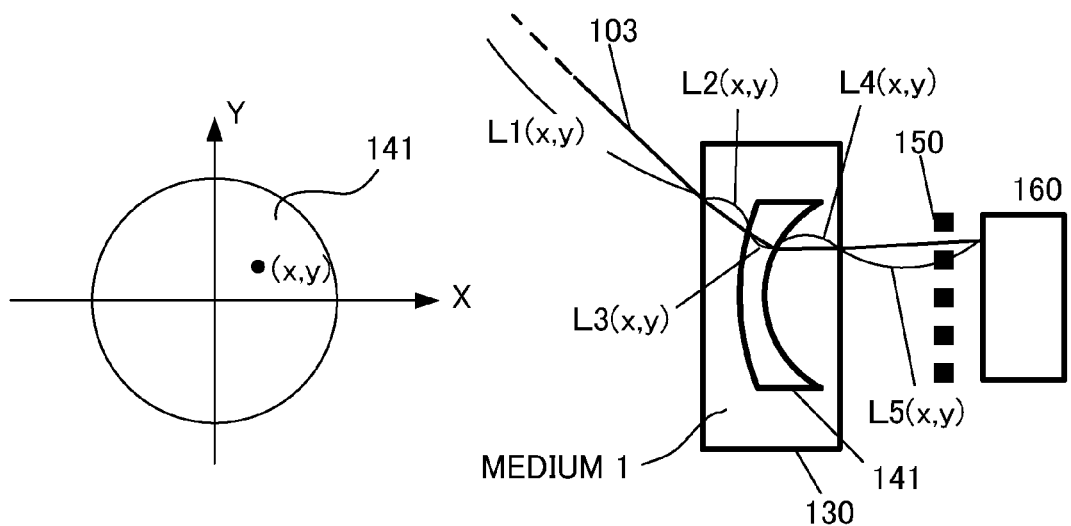
FIGS. 3A-3B are views for illustrating a coordinate system set in a reference object and an optical path of a ray in the refractive index distribution measuring apparatus according to the first embodiment.

Here, L1 to L5 are geometric distances among the components along the ray 103 as illustrated in FIG. 3B. The ray 103 schematically illustrates a ray that passes a point (x, y) in the reference object 141 illustrated in FIG. 3A. $N_1$ denotes a refractive index of air, and Ng denotes an ideal refractive index of the reference object 141. The reference object 141 is contemplated by replacing the refractive index distribution of the object 140 with a known value. In order to simplify the expression, a thickness of the wall of the container 130 is ignored.

Next, while the object 140 is immersed in the air, the (first) transmitted wavefront $W_m$ of the object 140 in the first medium is measured (measuring step) (S204). S204 contains an acquisition of an image of the interference pattern by the image-pickup element 180 and an image restoration of the transmitted wavefront by the processor 200. The image restoration of the transmitted wavefront (referred to as a "wavefront restoration" hereinafter) is performed by the fast Fourier transform ("FFT") method.

The wavefront restoration by the FFT method is a method that separates the aberration from the carrier pattern by utilizing a characteristic in that the aberration disturbs the carrier pattern of the interference pattern. More specifically, the two-dimensional FFT is performed for the interference pattern, and the interference pattern is converted into the frequency map. Next, the inverse fast Fourier transform (iFFT) method is performed after only part near the carrier frequency is picked up in the frequency map and a coordinate transformation is performed so as to set the carrier frequency to the origin. Thereby, a phase term of the complex amplitude is found. The resultant phase map becomes the transmitted wavefront.

$W_m$ are expressed as follows using L1 to L5:

$W_m(x,y)=OP_m(x,y)-OP_m(0,0)$ $OP_m(x,y)=L1(x,y)+L2(x,y)N_1+\{L3(x,y)+dL\}$
$N(x,y)+\{L4(x,y)-dL\}N_1+L5(x,y)$ Expression 4

Here, the N bar is a refractive index distribution projected value averaged in the optical path direction of the object 140 at the coordinate (x, y), and dL denotes a thickness error of the object 140 at the coordinate (x, y).

Next, the (first) wavefront aberration W1 corresponding to a difference between the simulation wavefront $W_{sim}$ and the transmitted wavefront $W_m$ is found by utilizing the following expression (S205). In order to simply the expression, the refractive index Ng is assumed to be equal to the refractive index N(0, 0) on the optical axis of the object 140:

$$W1 = W_m - W_{sim} = L3(x,y)\{\overline{N}(x,y) - Ng\} + dL(x,y)\{\overline{N}(x,y) - N_1\} - dL(0,0)\{Ng - N_1\} \quad \text{Expression 5}$$

S203 is independent of S202 or S204, and may be executed at any timing between S201 to S205.

Next, while the medium 2 (water) as a second medium having a second refractive index is filled in the container 130, the object 140 is installed in the container 130 (S30). Next, in accordance with the above step A, the (second) wavefront aberration W2 of the object 140 is measured (measuring step) (S40), where $N_2$ denotes the refractive index of water. At this time, the measuring step in S204 measures the (second) transmitted wavefront $W_m$ of the object 140 in the second medium while the object 140 is immersed in water (S204).

$$W2 = W_m - W_{sim} = L3(x,y)\{\overline{N}(x,y) - Ng\} + dL(x,y)\{\overline{N}(x,y) - N_2\} - dL(0,0)\{N_g - N_2\} \quad \text{Expression 6}$$

Next, the refractive index distribution projected value of the object 140 is calculated by removing the shape component dL of the object 140 from the wavefront aberration W1 and the wavefront aberration W2 (S50). S50 is the calculating step for obtaining the refractive index distribution projected vale containing information of the refractive index distribution of the object 140 by removing the influence of the shape error of the object using the two wavefront aberrations W1 and W2 of the object arranged at the same position. Here, an approximation of Expression 8 is used.

$$\overline{N}(x,y) = Ng + \frac{1}{L3(x,y)} \times \frac{(Ng-N_1)W2 - (Ng-N_2)W1}{N_2 - N_1} \quad \text{Expression 7}$$

$$\{\overline{N}(x,y) - Ng\}dL(x,y) \approx 0 \quad \text{Expression 8}$$

Thereby, a refractive index distribution projected value is found at a first object inclination relative to the object 140, which is an inclination in a case in which the optical axis accords with a rotationally symmetrical axis of the object 140. Since the refractive index distribution projected value is a refractive index averaged in the optical path direction of the light incident upon the object 140, it is necessary to find the refractive index distribution projected value by introducing the light into the object 140 at an inclination different from the first object inclination so as to obtain three-dimensional refractive index distribution information. A description will now be given of this method.

In order to find the refractive index distribution projected values of the object 140 with a plurality of orientations of the object 140, the object 140 is rotated and decentered (S61). The measurement number of S60 is different according to the refractive index distribution to be found. When it can be assumed that the object 140 has a rotationally symmetrical shape around an axis and the refractive index distribution is rotationally symmetrical around the same axis, the measurement number may be twice. For example, an orientation (first object inclination) in a case in which the optical axis is accorded with the rotationally symmetrical axis of the object 140, and an orientation (second object inclination) in a case in which an optical axis is no accorded with the rotationally symmetrical axis of the object 140.

Figures 4A, 4B:
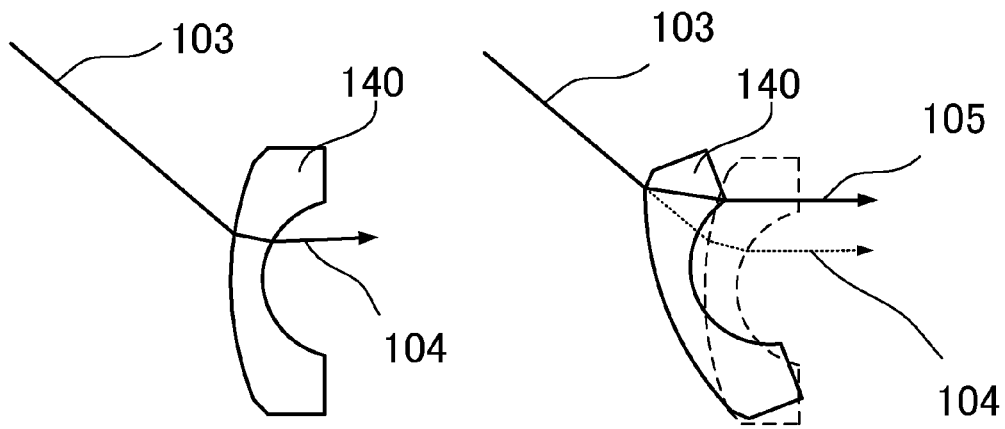
FIGS. 4A-4B are views for illustrating an inclination of the object according to the first embodiment.

FIG. 4A illustrates the first object inclination and FIG. 4B illustrates the second object inclination in this embodiment. In the first object inclination, the incident ray 103 and the exit ray 104 for the object 140 are as illustrated in FIG. 4A, and in the second object inclination, the incident ray 103 and the exit ray 105 are as illustrated in FIG. 4B.

In order to precisely obtain three-dimensional refractive index distribution information by the small measurement number, a plurality of measurement orientations of the refractive index distribution projected value may be made greatly different from each other. In other words, the first object inclination and the second object inclination may be made greatly different from each other. The second object inclination may be adjusted so that the incident ray 103 can pass the ends of the first surface and the second surface of the object 140, as illustrated in FIG. 4B. The end of the first surface is a boundary between the cutting surface and the R surface of the first surface as the optical surface on the light incidence side of the object, and the end of the second surface is a boundary between the cutting surface and the R surface of the second surface as the optical surface on the light exit side of the object.

This embodiment parallel moves and decenters the object 140 relative to the optical axis direction and rotates the object 140 around an axis perpendicular to the optical axis in S61 and arranges the object 140 at a position and angle as illustrated in FIG. 4B.

After S61, S10 to S50 are again performed until the measurement number for calculating the refractive index distribution projected value reaches the designated number (which is twice in this embodiment) in S60.

When the measurement number reaches the designated number, the three-dimensional refractive index distribution is calculated from a plurality of obtained refractive index distribution projected values (S70). S70 is the calculating step for obtaining information of the three-dimensional refractive index distribution based on a plurality of refractive index distribution projected values corresponding to a plurality of different orientations of the object 140. The three-dimensional refractive index distribution is calculated by determining the polynomial coefficients that express the three-dimensional refractive index distribution so that a plurality of calculated refractive index distribution projected values can be reproduced.

When the incident ray 103 is expressed by 100 rays, the refractive index distribution projected values are expressed as follows:

$$\overline{N}_1 = \begin{pmatrix} n_1 \\ \vdots \\ n_{100} \end{pmatrix} \overline{N}_2 = \begin{pmatrix} n_{101} \\ \vdots \\ n_{200} \end{pmatrix} \overline{N} = \begin{pmatrix} \overline{N}_1 \\ \overline{N}_2 \end{pmatrix} \quad \text{Expression 9}$$

The $N_1$ bar and the $N_2$ bar are refractive index distribution projected values at the first and second object inclinations. In addition, assume that the three-dimensional refractive index distribution P to be found is expressed by twelve polynomial coefficients.

$$1 : p_1, r^2 : p_2, r^4 p_3, r^6 : p_4,$$
$$z : p_5, zr^2 : p_6, zr^4 : p_7, zr^6 : p_8,$$
$$z^2 : p_9, z^2r^2 : p_{10}, z^2r^4 : p_{11}, z^2r^6 : p_{12} \quad \text{Expression 10}$$

$$P = \begin{pmatrix} p_1 \\ \vdots \\ p_{12} \end{pmatrix}$$

When it is assumed that U is a refractive index distribution projected value using polynomial coefficients of Expression 10 as a unit amount, U can be expressed by the following expression:

$$U = \begin{pmatrix} u_{1,1} & \cdots & u_{12,1} \\ \vdots & & \vdots \\ u_{1,200} & \cdots & u_{12,200} \end{pmatrix} \quad \text{Expression 11}$$

Each coefficient of P can reproduce the plurality of found refractive index distribution projected values when P is determined so as to satisfy the following equate.

$$\overline{N} = UP \quad \text{Expression 12}$$

When the least-squares method is used, $\Phi$ is defined as in Expression 13 and each coefficient of P is determined so that $\Phi^2$ can be least.

$$\Phi = UP - \overline{N} \quad \text{Expression 13}$$

P can be directly found as in Expression 14 by finding $U^{-1}$ when the eigenvalue decomposition is used.

$$P = U^{-1}\overline{N} \quad \text{Expression 14}$$

Alternatively, a combination method may be used which defines $\Phi$ as a value made by subtracting a right side value from a left side value in Expression 14 and determines each coefficient of P so that $\Phi^2$ can be least or another known method may be used to find P. Thus, a refractive index distribution measuring method ends in this embodiment by finding a three-dimensional refractive index distribution P.

As discussed above, this embodiment measures two types of wavefront aberrations of the object utilizing two types of media and the reference light emitted from the light source, obtains the refractive index distribution projected values by removing the shape component of the object from the wavefront aberration, and acquires another refractive index distribution projected value by changing an angle of the object relative to the optical axis. The polynomial coefficients which express the three-dimensional refractive index distribution of the object are found based on a plurality of refractive index distribution projected values. Thereby, even when a refractive index of the object is high, an internal refractive index distribution of the object can be highly precisely measured by utilizing a medium having a refractive index that is lower than the refractive index of the object.

For simple description, this embodiment properly sets the number of rays that expresses the incident rays 103 and a polynomial that expresses the three-dimensional refractive index distribution. More specifically, the incident light is expressed as one ray, and the measurement designated number of the refractive index distribution projected value is set to m and the polynomial that expresses the refractive index distribution has n terms. Even in this case, P can be found by a method similar to Expression 12 by setting the refractive index distribution projected value N bar, the refractive index distribution P, and the refractive index distribution projected value U of a case where each coefficient of P has a unit amount as in Expression 15:

$$\overline{N} = \begin{pmatrix} n_1 \\ \vdots \\ n_{1m} \end{pmatrix} \quad P = \begin{pmatrix} p_1 \\ \vdots \\ p_n \end{pmatrix} \quad U = \begin{pmatrix} u_{1,1} & \cdots & u_{n,1} \\ \vdots & & \vdots \\ u_{1,1n} & \cdots & u_{n,1m} \end{pmatrix} \quad \text{Expression 15}$$

As in this embodiment, a large aberration caused by a refractive index difference between the object and the medium can be measured by using the Talbot interferometer for the measuring unit. The Talbot interferometer is one type of a lateral shearing interferometer configured to measure as an interference pattern a difference between the transmitted wavefront and its sheared transmitted wavefront.

The shearing interferometer is a measuring unit configured to find an amount corresponding to a gradient of a wavefront shape of the transmitted wavefront. A lateral shift amount of the transmitted wavefront is referred to as a shear amount, and a ratio of the shear amount to the diameter of the light is referred to as a shear ratio. By reducing a shear ratio, a large transmitted wavefront aberration can be measured as a small aberration (shear wavefront) that does not make dense the interference pattern.

In general, when the shear ratio is excessively small in the shearing interferometer, the shear wavefront is embedded in the noises and the precision deteriorates. Thus, the shear ratio may be 3 to 5% as large as the diameter of the pupil. However, this embodiment sets the shear ratio to 1.5% or smaller, e.g., about 0.4 to 0.9% so as to measure the transmitted wavefront having a large aberration with a small shear wavefront.

The shear ratio is defined as $(\lambda Z)/(dD)$ using a Talbot distance Z and a diameter D of the interference pattern data on the image-pickup element 180, and is defined as (md)/D using Expression 2 and the diameter $D_0$ of the light flux on the diffraction grating 170. Therefore, the shear ratio is proportional to the grating pitch of the diffraction grating 170. From Expression 2, the pitch of the diffraction grating 170 affects the Talbot distance Z, and it is thus necessary to determine the pitch by considering the interference among the components in the measuring apparatus. For example, if it is assumed that $D_O$ is about 10 to 20 mm when m=1, the grating pitch may be about 40 to 180 µm.

While this embodiment set two types of media to air and water, the medium is not limited as long as two types of media are different by 0.01 or higher. In addition, the two types of media may be made from the same material having different refractive indexes by changing its temperature.

While this embodiment discusses use of the Talbot interferometer, a lateral shearing interferometer, and a radial shearing interferometer, and another shearing interferometer different from the Talbot interferometer may be used.

Second Embodiment

Figure 5:
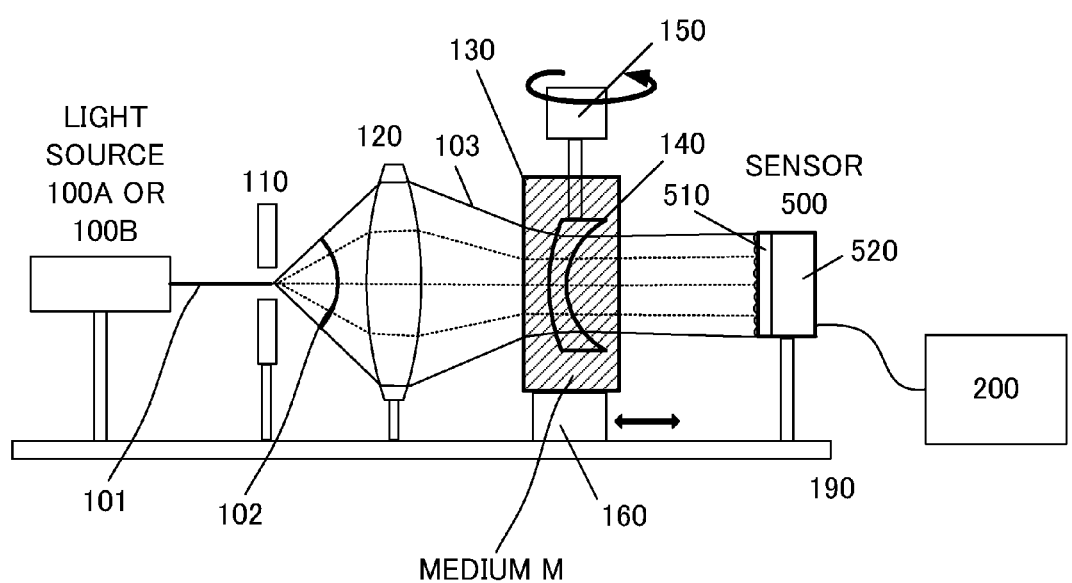
FIG. 5 is a block diagram of a refractive index distribution measuring apparatus according to a second embodiment.

FIG. 5 is a block diagram of a refractive index distribution measuring apparatus of the second embodiment. The refractive index distribution measuring apparatus of this embodiment finds a refractive index distribution by measuring the transmitted wavefront twice using two types of light sources and one type of medium M. The two types of light sources are, for example, a He—Ne laser (with a first wavelength of 633 nm) as a light source 100A and a second harmonic of a YAG laser (with a second wavelength of 532 nm different from the first wavelength) as a light source 100B.

The medium M has a refractive index different from that of the object 140. For example, the refractive index of the medium is smaller than that of the object, and larger than that of air. One example of the medium M is water, and low refractive index oil having a refractive index of about 1.5 to about 1.8.

The pinhole plate 110 generates (reference) light having the ideal spherical wave using a laser beam emitted from the light source 100A or 100B. This light passes the object 140 similar to FIG. 1, and its transmitted wavefront is measured by a Shack-Hartman sensor 500 as a wavefront measuring sensor. The Shack-Hartman sensor 500 includes, in order from the light source along the optical path, a lens array 510 and an image pickup element 520.

Similar to the first embodiment, the collimator lens 120, the container 130, and the sensor 500 are arranged on the rail (not illustrated) parallel to the optical axis. The light incident upon the object 140 can be converted into any one of the divergent light, collimated light, and the convergent light by moving these components on the rail. Thereby, the NA of the light flux incident upon the Shack-Hartman sensor 500 can be adjusted.

In comparison with the Talbot interferometer, the Shack-Hartman sensor requires the NA of the light flux incident upon the sensor to be strictly controlled but the alignment of the sensor 500 becomes easier because it is unnecessary to set an interval between the diffraction grating 170 and the CCD 160 to the Talbot distance.

The Shack-Hartman sensor 500 condenses the light incident upon the lens array 510 upon the CCD. When the inclined transmitted wavefront is incident upon the lens array 510, a position of the condensing point shifts. Since the Shack-Hartman sensor 500 can convert an inclination of the transmitted wavefront into a positional shift of the condensing point and measure the positional shift, a wavefront having a large aberration can be measured.

Figure 6:
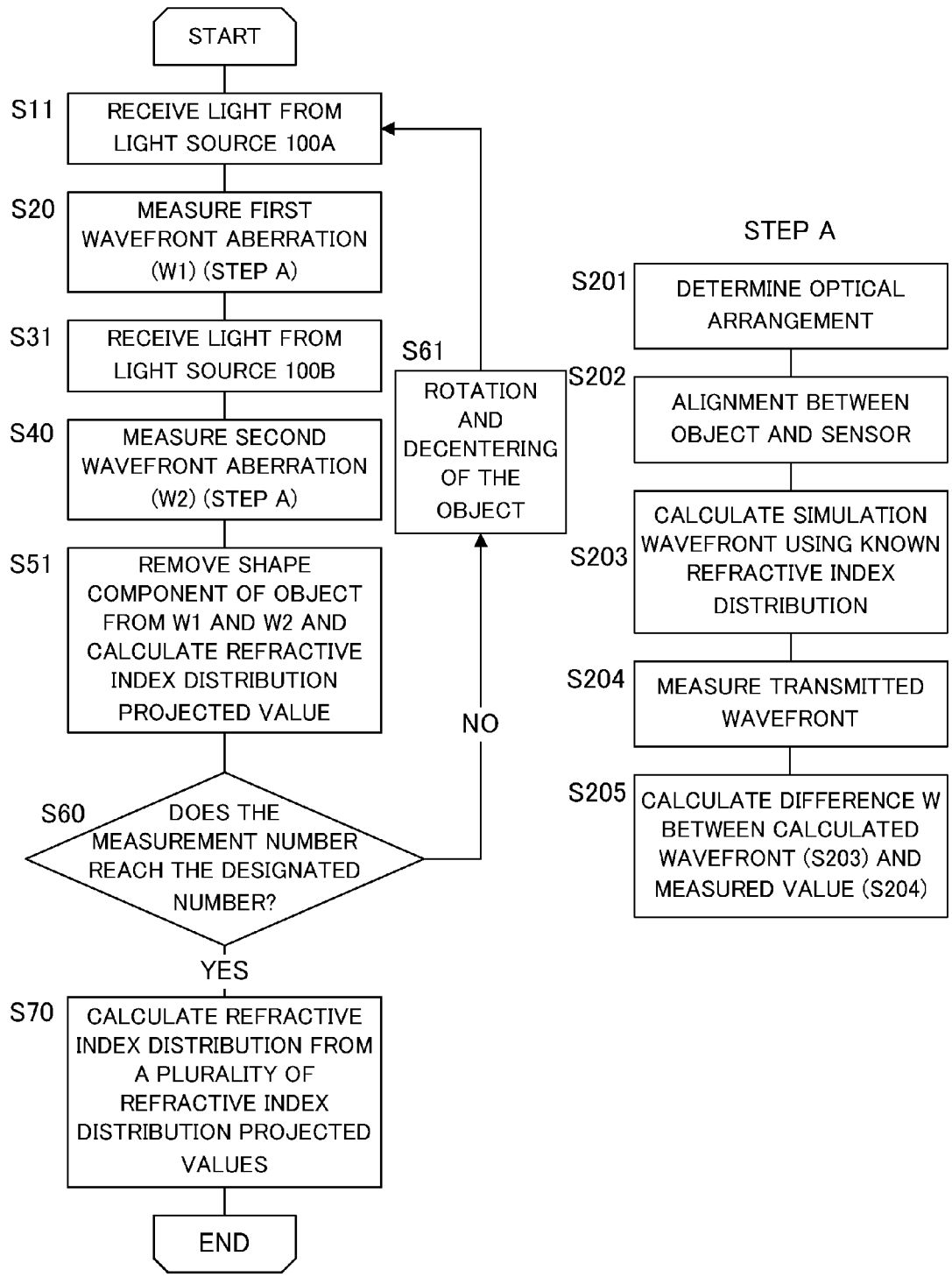
FIG. 6 is a flowchart for illustrating a refractive index distribution measuring method according to the second embodiment.

FIG. 6 is a flowchart for illustrating a refractive index distribution measuring method of this embodiment, and "S" stands for the step. The refractive index distribution measuring method is executed as a computer program by the processor 200, such as a microcomputer illustrated in FIG. 5. Most of the flow of FIG. 6 is the same of the measurement flow in FIG. 2, and thus only the difference will be discussed.

Initially, light from the light source 100A is introduced into the pinhole plate 110 (S11), and the wavefront aberration W1 using the first wavelength is measured (S20). Next, light from the light source 100B having a wavelength different from that of the light source 100A is introduced into the pinhole plate 110 (S31), and the wavefront aberration W2 is measured (S40). The wavefront aberrations obtained in these steps are expressed by the following expressions:

$$W1 = L3(x,y)\{\overline{N}T_{HeNe}(x,y) - Ng_{HeNe}\} + dL(x,y)\{\overline{N}_{HeNe}(x,y) - N_{oilHeNe}\} - dL(0,0)\{Ng_{HeNe} - N_{oilHeNe}\}$$

$$W2 = L3(x,y)\{\overline{N}_{YAG}(x,y) - Ng_{YAG}\} + dL(x,y)\{\overline{N}_{YAG}(x,y) - N_{oilYAG}\} - dL(0,0)\{Ng_{YAG} - N_{oilYAG}\} \quad \text{Expression 16}$$

Here, the $N_{HeNe}$ bar and the $N_{YAG}$ bar are refractive index distribution projected values at a position (x, y) in the object for the first light source (He—Ne laser) and the second light source (YAG second harmonic), respectively. $Ng_{HeNe}$ and $Ng_{YAG}$ are ideal refractive indexes of the object (refractive indexes of the reference object) for respective light sources. $N_{oilHeNe}$ and $N_{oilYAG}$ are refractive indexes of the medium for the respective light sources.

The refractive index for the first light source and the refractive index for the second light source have the following approximation relationship:

$$\overline{N}_{YAG}(x, y) = \frac{Ng_{YAG} - 1}{Ng_{HeNe} - 1} \overline{N}_{HeNe}(x, y) \quad \text{Expression 17}$$

By utilizing Expressions 16 and 17, the refractive index distribution projected value can be found (S51).

$$\overline{N}_{HeNe}(x, y) = Ng_{HeNe} + \frac{1}{L3(x, y)} \times \frac{(Ng_{HeNe} - N_{oilHeNe})W2 - (Ng_{YAG} - N_{oilYAG})W1}{\frac{Ng_{YAG} - 1}{Ng_{HeNe} - 1}(Ng_{HeNe} - N_{oilHeNe}) - (Ng_{YAG} - N_{oilYAG})} \quad \text{Expression 18}$$

Thereafter, S60, S61, and S70 follow and the measurement ends.

In Expression 18, when $\Psi$ of Expression 20 is large, the errors of the measurement values W1 and W2 can be reduced.

$$\Psi = \frac{Ng_{YAG} - 1}{Ng_{HeNe} - 1}(Ng_{HeNe} - N_{oilHeNe}) - (Ng_{YAG} - N_{oilYAG}) \quad \text{Expression 19}$$

For example, when the medium is air, $N_{oil} \approx 0$ is satisfied. Thus, $\Psi \approx 0$ is established and the measurement becomes unavailable. In addition, for example, when it is assumed that the refractive index of the object does not greatly change as the wavelength changes, $Ng_{YAG} \approx Ng_{HeNe}$ is established and thus Expression 19 can be expressed as Expression 20.

$$\Psi = N_{oilYAG} - N_{oilHeNe} \quad \text{Expression 20}$$

In this case, a medium having a large refractive index difference may be selected between the first light source and the second light source. In order to increase $\Psi$, the medium needs to be determined by considering the refractive index of the object.

The measuring apparatus of this embodiment may be one that can measure an amount corresponding to a gradient of a wavefront shape of the transmitted wavefront or an inclination of the ray, and that can detect the gradient or inclination as a measurable physical amount, even when the transmitted wavefront has a large aberration. Therefore, the measuring apparatus is not limited to the Shack-Hartman method and may use the Hartman method or the Ronchi test.

The result measured by the refractive index distribution measuring apparatuses or methods according to the first and second embodiments is applicable to the manufacturing method of the optical element. A method for manufacturing an optical element includes the steps of molding an optical element based on a designed optical element, measuring a shape of the molded optical element, evaluating the shape precision, and evaluating the optical performance of the optical element that satisfies the shape precision. The refractive index distribution measuring method of this embodiment is applicable to the step of evaluating the optical performance. When the evaluated optical performance does not satisfy the required specification, a correction amount of an optical surface of the optical element is calculated and the optical element is redesigned by using the result. When the evaluated optical performance satisfies the required specification, the optical element is mass-produced.

Since the manufacturing method of the optical element of this embodiment can highly precisely measure an internal refractive index distribution of the optical element, the optical element can be precisely mass-produced through molding even when the optical element is made of a high refractive index glass material.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-119636, filed May 25, 2010, which is hereby incorporated by reference herein in its entirety.

What is claimed is:

1. A refractive index distribution measuring method comprising the steps of:
   measuring a transmitted wavefront of an object by arranging the object in a medium having a refractive index different from that of the object, and by introducing reference light into the object; and
   calculating a refractive index distribution of the object by using a measurement result of the transmitted wavefront,
   wherein in a plurality of orientations of the object in the medium which are different from each other, the measuring step measures a first transmitted wavefront in a first medium having a first refractive index and a second transmitted wavefront in a second medium having a second refractive index different from the first refractive index; and
   wherein the calculating step obtains a refractive index distribution projected value of the object in each of the plurality of orientations by removing a shape component of the object utilizing measurement results of the first transmitted wavefront and the second transmitted wavefront and each transmitted wavefront of a reference object that has the same shape as that of the object and a specific refractive index distribution and is located in one of the first medium and the second medium with the same orientation as that of the object, and the calculating step calculates a three-dimensional refractive index distribution of the object based on a plurality of refractive index distribution projected values corresponding to the plurality of orientations.

2. The refractive index distribution measuring method according to claim 1, wherein the plurality of orientations include an orientation in which an incident ray upon the object passes a boundary between an optical surface and a cutting surface of the object on a light incidence side of the object and a boundary between an optical surface and a cutting surface of the object on a light exit side of the object.

3. A refractive index distribution measuring method comprising the steps of:
   measuring a transmitted wavefront of an object by arranging the object in a medium having a refractive index different from that of the object, and by introducing reference light into the object; and
   calculating a refractive index distribution of the object by using a measurement result of the transmitted wavefront,
   wherein in a plurality of orientations of the object in the medium, the measuring step measures a first transmitted wavefront for a first wavelength and a second transmitted wavefront for a second wavelength different from the first wavelength; and
   wherein the calculating step obtains a refractive index distribution projected value of the object in each of the plurality of orientations by removing a shape component of the object utilizing measurement results of the first transmitted wavefront for the first wavelength and the second transmitted wavefront for the second wavelength and each transmitted wavefront of a reference object that has the same shape as that of the object and a specific refractive index distribution and is located in the medium with the same orientation as that of the object, and the calculating step calculates a three-dimensional refractive index distribution of the object based on a plurality of refractive index distribution projected values corresponding to the plurality of orientations.

4. The refractive index distribution measuring method according to claim 3, wherein the plurality of orientations include an orientation in a case in which an incident ray upon the object passes a boundary between an optical surface and a cutting surface of the object on a light incidence side of the object and a boundary between an optical surface and a cutting surface of the object on a light exit side of the object.

5. A method for manufacturing an optical element, said method comprising the steps of:
   molding an optical element; and
   evaluating an optical performance of a molded optical element, by measuring a refractive index distribution of the optical element utilizing a refractive index distribution measuring method comprising the steps of:
   measuring a transmitted wavefront of an object by arranging the object in a medium having a refractive index different from that of the object, and by introducing reference light into the object; and
   calculating a refractive index distribution of the object by using a measurement result of the transmitted wavefront,
   wherein in a plurality of orientations of the object in the medium which are different from each other, the measuring step measures a first transmitted wavefront in a first medium having a first refractive index and a second transmitted wavefront in a second medium having a second refractive index different from the first refractive index; and
   wherein the calculating step obtains a refractive index distribution projected value of the object in each of the plurality of orientations by removing a shape component of the object utilizing measurement results of the first transmitted wavefront and the second transmitted wavefront and each transmitted wavefront of a reference object that has the same shape as that of the object and a specific refractive index distribution and is located in one of the first medium and the second medium with the same orientation as that of the object, and the calculating step calculates a three-dimensional refractive index distribution of the object based on a plurality of refractive index distribution projected values corresponding to the plurality of orientations.

6. A refractive index distribution measuring apparatus comprising:
   a light source;
   an adjuster configured to adjust an orientation of an object in a medium having a refractive index different from that of the object;
   a measuring unit configured to measure a transmitted wavefront of the object arranged in the medium, by utilizing light from the light source; and
   a processor configured to calculate a refractive index distribution of the object by using the transmitted wavefront,
   wherein in a plurality of orientations of the object in the medium which are different from each other, the measuring unit measures a first transmitted wavefront in a first medium having a first refractive index and a second transmitted wavefront in a second medium having a second refractive index different from the first refractive index; and wherein the processor obtains a refractive index distribution projected value of the object in each of the plurality of orientations by removing a shape component of the object utilizing measurement results of the first transmitted wavefront and the second transmitted wavefront and each transmitted wavefront of a reference object that has the same shape as that of the object and a specific refractive index distribution and is located in one of the first medium and the second medium with the same orientation as that of the object, and the processor calculates a three-dimensional refractive index distribution of the object based on a plurality of refractive index distribution projected values corresponding to the plurality of orientations.

7. The refractive index distribution measuring apparatus according to claim 6, wherein the measuring unit includes a shearing interferometer.

8. The refractive index distribution measuring apparatus according to claim 6, wherein the measuring unit includes a Shack-Hartman sensor.

9. A refractive index distribution measuring apparatus comprising:
a light source configured to emit light with a first wavelength and light with a second wavelength;
an adjuster configured to adjust an orientation of an object in a medium having a refractive index different from that of the object;
a measuring unit configured to measure a transmitted wavefront of an object arranged in the medium, by utilizing light from the light source; and
a processor configured to calculate a refractive index distribution of the object based on the first transmitted wavefront measured with the first wavelength and second transmitted wavefront measured with the second wavelength,
wherein in a plurality of orientations of the object in the medium, the measuring unit measures a first transmitted wavefront for a first wavelength and a second transmitted wavefront for a second wavelength different from the first wavelength; and
wherein the processor obtains a refractive index distribution projected value of the object in each of the plurality of orientations by removing a shape component of the object utilizing measurement results of the first transmitted wavefront and the second transmitted wavefront and each transmitted wavefront of a reference object that has the same shape as that of the object and a specific refractive index distribution and is located in the medium with the same orientation as that of the object, and the processor calculates a three-dimensional refractive index distribution of the object based on a plurality of refractive index distribution projected values corresponding to the plurality of orientations.

10. The refractive index distribution measuring apparatus according to claim 9, wherein the measuring unit includes a shearing interferometer.

11. The refractive index distribution measuring apparatus according to claim 9, wherein the measuring unit includes a Shack-Hartman sensor.

* * * * *